US009188591B2

(12) United States Patent
Bergmann et al.

(10) Patent No.: US 9,188,591 B2
(45) Date of Patent: Nov. 17, 2015

(54) USE OF PRECURSORS OF TACHYKININS AND/OR THEIR FRAGMENTS IN MEDICAL DIAGNOSTIC

(75) Inventors: Andreas Bergmann, Berlin (DE); Andrea Ernst, Hennigsdorf (DE)

(73) Assignee: SPHINGOTEC GMBH, Hennigsdorf (DE)

( * ) Notice: Subject to any disclaimer, the term of this patent is extended or adjusted under 35 U.S.C. 154(b) by 648 days.

(21) Appl. No.: 12/939,390

(22) Filed: Nov. 4, 2010

(65) Prior Publication Data

US 2011/0275091 A1 Nov. 10, 2011

Related U.S. Application Data

(62) Division of application No. 11/568,146, filed as application No. PCT/EP2005/004254 on Apr. 20, 2005, now Pat. No. 7,838,245.

(30) Foreign Application Priority Data

Apr. 20, 2004 (EP) .............................. 20040009284

(51) Int. Cl.
*G01N 33/68* (2006.01)

(52) U.S. Cl.
CPC ............ *G01N 33/68* (2013.01); *G01N 33/6872* (2013.01); *G01N 2410/06* (2013.01); *G01N 2500/04* (2013.01)

(58) Field of Classification Search
None
See application file for complete search history.

(56) References Cited

U.S. PATENT DOCUMENTS

| 5,268,359 A | 12/1993 | Harmar et al. |
| 5,882,864 A * | 3/1999 | An et al. ........................ 435/6.14 |
| 6,358,941 B1 * | 3/2002 | Snorrason et al. ............. 514/183 |
| 6,812,339 B1 | 11/2004 | Venter et al. ................ 536/24.31 |
| 7,838,245 B2 | 11/2010 | Bergmann et al. |
| 2003/0077658 A1 * | 4/2003 | Wells ............................. 435/7.1 |
| 2003/0114763 A1 * | 6/2003 | Reddy et al. ................... 600/483 |
| 2006/0053498 A1 | 3/2006 | Bejanin et al. ..................... 800/8 |

FOREIGN PATENT DOCUMENTS

| EP | 1241257 | 9/2002 |
| WO | 87/07643 | 12/1987 |
| WO | 02/103016 | 12/2002 |
| WO | WO 03025547 A1 * | 3/2003 | ............ G01N 21/01 |
| WO | WO 2004031238 A2 * | 4/2004 | ............ C07K 16/00 |
| WO | 2004/076614 | 9/2004 |
| WO | WO 2005043111 A2 * | 5/2005 |

OTHER PUBLICATIONS

Kage et al., N-Flanking Peptide of Protachykinin-A (Protachykinin [1-37]) in Plasma of Patients with Carcinoid Syndrome-Comparison with Substance P, Digestion 46 (Supp. 1), p. 50, 1990.*

Kage et al., Post-translational processing of preprotachykinins, Biochem J., 1988, 253, 203-207.*
Kuriyama et al, Cell Motility and the Cytoskeleton 30:171-182, 1995.*
Fremont et al., Acute Lung Injury in Patients with Traumatic Injuries: Utility of Panel of Biomarkers for Diagnosis and Pathogensis, J. Trauma. May 2010; 68(5): 1121-1127.*
Drynda et al., Proteome analysis reveals disease-associated marker proteins to differentiate RA patients from other inflammatory joint diseases with the potential to monitor anti-TNF-alpha therapy, Pathology Research and Practice, 200 (2004) 165-171.*
Luepker et al., Case Definitions for Acute Coronary Heart Disease in Epidemiology and Clinical Research Studies, Circulation. 2003;108:2543-2549.*
Toikka et al., Serum procalcitonin, C-reactive protein and interleukin-6 for distinguishing bacterial and viral pneumonia in children, Pediatric Infectious Disease Journal: 19(7), 2000 abstract.*
Schwarz et al., Serum procalcitonin levels in bacterial and abacterial meningitis, Critical Care Medicine, 28(6), 2000 abstract.*
Boschetto, Sputum substance P and neurokinin A are reduced during exacerbations of chronic obstructive pulmonary disease, Pulmonary Pharmacology & Therapeutics 18 (2005) 199-205.*
Ronald et al, The evolution of immunoassay technology, Parasitology (1998), 117, S13-S27.*

(Continued)

*Primary Examiner* — Galina Yakovleva
*Assistant Examiner* — Andrea S Grossman
(74) *Attorney, Agent, or Firm* — Heslin Rothenberg Farley & Mesiti P.C.

(57) ABSTRACT

The present invention relates to the use of protachykinin and/or fragments thereof that can be isolated from body fluids, tissues or other biological samples and therefore, serves as a marker peptide for medical diagnosis of diseases/disorders of the central nervous system, including Alzheimer's disease, Parkinson's disease, depression and/or conditions of pain, neurological, endocrinological, cerebral, muscular, local, systemic, chronic, inflammatory diseases, infectious diseases comprising bacterial and viral infections, meningitis, sepsis, Crohn's disease, colitis ulcerosa, sickle cell anemia, ischemia, amyotrophic lateral sclerosis, arthritis comprising rheumatoid arthritis, bronchitis, hyperalgesia, asthma, intoxication comprising bacterial intoxication, immunological disorders, poly/-trauma comprising craniocerebral trauma, tumors/cancer, stroke, stress, atopis dermatitis, HIV, Huntington's disease, burns, schizophrenia, Hirschsprung's disease, allergies, familial dysautononmia (Riley Day syndrome), hematopoietic disorders, gliomas comprising glioblastomas and astrocytomas, disorders of the blood brain barrier. The invention further provides antibodies for binding to certain proteins and their fragments, more specifically protachykinin and protachykinin peptides. In accordance with the invention, a kit useful for the above-mentioned diagnosis is also provided.

9 Claims, 14 Drawing Sheets

(56) References Cited

OTHER PUBLICATIONS

Yokoyama et al., Production of Monoclonal Antibodies, in Current Protocols in Immunology, Supplement 71, (2006) 2.5.1-2.5.25.*

Toresson et al., N-terminally extended tachykinins in human cerebrospinal fluid, Regulatory Peptides, 46 (1993) 357-359.*

Rosier et al., Clinical significance of neurobiochemical profiles in the lumbar cerebrospinal fluid of Alzheimer's disease patients, J Neural Transm (2001) 108:231-246.*

Anderson, The Clinical Plasma Proteome: A Survey of Clinical Assays for Proteins in Plasma and Serum, Clinical Chemistry, 56:2, 177-185 (2010).*

International Search Report for corresponding European Patent Application EP2005/004254.

Dandona et al., "Procalcitonin Increase after Endotoxin Injection in Normal Subjects", Journal of Clinical Endocrinology and Metabolism, 1994, vol. 79(5), 1605-1608.

The Sanger Centre. Genome Research. 1998. vol. 8:1097-1108.

Theodorsson-Norheim et al., Eur. J. Biochem. 166. pp. 6930698. 1987.

Harmar et al., FEBS 4102. vol. 208, No. 1. Nov. 1986, pp. 67-72.

* cited by examiner

USE OF PRECURSORS OF TACHYKININS AND/OR THEIR FRAGMENTS IN MEDICAL DIAGNOSTIC

CROSS-REFERENCE TO RELATED APPLICATIONS

This application is a divisional of co-pending U.S. application Ser. No. 11/568,146, filed Oct. 20, 2006, which is a §371 filing of International Application PCT/EP2005/004254, filed Apr. 20, 2005 (published as WO 05/103712), which claims priority from European Application No. 20040009284 filed Apr. 20, 2004. The entire content of each of the prior applications is incorporated herein by reference.

The present invention relates to the use of protachykinin and/or its fragments and/or its splice variants, fragments comprising protachykinin and/or combinations thereof in medical diagnostics. In the following text all these molecules, fragments, combinations thereof etc. are referred to as protachykinin comprising for example also preprotachykinin and the amino acid sequence IDs 1-10.

Protachykinin can be used to diagnose a variety of diseases comprising diseases/disorders of the central nervous system, comprising Alzheimer's disease, Parkinson's disease, depression and/or conditions of pain, neurological, endocrinological, cerebral, muscular, local, systemic, chronic, inflammatory diseases, infectious diseases comprising bacterial and viral infections, meningitis, sepsis, Crohn's disease, colitis ulcerosa, sickle cell anemia, ischemia, amyotrophic lateral sclerosis, arthritis comprising rheumatoid arthritis, bronchitis, hyperalgesia, asthma, intoxication comprising bacterial intoxication, immunological disorders, poly/-trauma comprising cranio-cerebral trauma, tumors/cancer, stroke, stress, atopis dermatitis, HIV, Huntington's disease, burns, fibromyalgy, schizophrenia, Hirschsprung's disease, allergies, familial dysautononmia (Riley Day syndrome), hematopoietic disorders, gliomas comprising glioblastomas and astrocytomas, disorders of the blood brain barrier.

The term protachykinin of the present invention comprises also amino acid sequences showing at least 75% homology, preferred at least 80% homology, more preferred at least 90% homology to protachykinin or fragments of PTK in the above sense.

The invention further relates to antibodies raised against protachykinin and/or its fragments and/or its splice variants and kits involving such components.

BACKGROUND OF THE INVENTION

In 1931, the undecapeptide substance P was isolated by Von Euler and Gaddum (Von Euler and Gaddum, 1931). It was named Substance P because of its powdery consistency (Gaddum and Schild, 1934). Substance P (SP) is encoded by the preprotachykinin A-gene (PPT-A) which also comprises the gene sequences of other tachykinins like Neurokinin A (NKA), Neuropeptide K (NPK) and Neuroptid γ (NP γ) (Carter and Krause, 1990). Neurokinin B is encoded by the PPT II or PPT-B gene. Substance P is expressed in the central nervous system (CNS) as well as in the peripheral nervous system (PNS) (Otsuka and Yoshioka, 1993).

Tachykinins have a variety of functions. They have vasodilatory properties, are responsible for the contraction and relaxation of the smooth muscles in the gastro-intestinal and urogenital tract as well as in the bronchi. Furthermore, tachykinins play a major role in reflexes of defense caused by injuries or conditions of pain. These are, for example, the increase in cardiovascular tonus, vasodilation and triggering the NO-biosynthesis. Substance P has an influence on different inflammatory cells, serves as a neurotransmitter for transmitting pain and has regulatory function in blood formation. The non-Substance P-tachykinin Neurokinin A, Neuropeptide γ as well as Neuropeptide K are likely to play a role as regulators of endocrine functions.

The level of Substance P in body fluids is altered in several diseases. In plasma of sepsis patients a significant increase of the concentration of Substance P was shown well as in plasma and synovial fluid of patients with rheumatoid arthritis (Joyce, Yood and Carraway, 1993).

Substance P also seems to play a role in inflammatory intestinal diseases like Crohn's disease and colitis ulcerosa.

Substance P m-RNA expression is significantly increased in HIV-infected macro-phages, which indicates an effect of that tachykinin in HIV infections.

In the liquor of Alzheimer's patients (late-onset) and patients suffering from amyotrophic lateral sclerosis a significant increase of Substance P is observed.

In Parkinson's disease a reduction or an increase of Substance P in the medial globus pallidus was observed depending on the degree of dopamine reduction in the putamen.

Patients suffering from Chorea Huntington, a genetically dependent neuro-degenerative disease, showed a selective loss of preprotachykinin containing neurons in the brain.

In the serum of patients with cerebral ischemia (transient inhibition of blood flow as well as stroke), a significant increase in concentrations of Substance P could be determined.

Patients having carcinoid tumors showed an increased concentration of Substance P and Neurokinin A in the blood circulation as well as a significant increase in immune reactivity of tachykinin-like metabolites in urine. Substance P and Neurokinin A possibly also play a role in migraine, other subsistence disorders, in the development of glioma and they have a strong influence on the secretion in the bronchial tubes and on the bronchial circulation, which suggests that they might play a possible role as mediators in asthma.

In smokers suffering from a chronic bronchitis a ten-fold increase of PPT-A-mRNA concentration in lung epithelial cells could be shown.

In fibromyalgy and depression the concentration of Substance P in serum and liquor is increased, as well as in serum of patients suffering from sickle cell anemia is increased, especially in phases of pain.

Increased concentrations of Substance P are measured in patients suffering from atopic dermatitis that correlate with the severity of the disease.

Tachykinins like Substance P and Neurokinin A furthermore play a role in the regulation of proinflammatory cytokine responses.

The biosynthesis of the tachykinins starts as preprohormone. During biosynthesis after separation of the hydrophobic N-terminal sequence by so-called signal peptidasis and folding of the proteins in the lumen of the endoplasmic reticulum, the propeptides migrate into the vesicles of the Golgi Apparatus and are transported to the cell membrane. During transport the propeptides are processed to mature hormones by prohormone-convertases at usually dibasic amino acid sequences. Via different stimuli the peptides are secreted into the extracellular space or into the plasma. The mature peptides are rapidly inactivated after secretion by proteolysis. Substance P and Neurokinin A in vivo have an extremely low half-life of less than 2 minutes in blood. Neuropeptide K shows a bi-phasic degradation with a half-life of 0.9 minutes (degradation to Neuropeptide γ) and 6 minutes in plasma (further degradation).

The tachykinin Substance P, Neurokinin A, Neuropeptide K and Neuropeptide γ are encoded by the preprotachykinin A-gene (PPT-A). Alternative splicing of the PPT-A gene transcript results in 4 different mRNA molecules: α PPT-A, β PPT-A, γPPT-A and δPPT-A. All four mRNA molecules contain the sequence of Substance P. Only βPPT-A mRNA contains all 7 exons of the PPTA-gene and thus encodes all 4 tachykinins. Exon 6 is missing in the α PPT-A mRNA and exons 4 and 6 are missing in the δPPT-A mRNA. Thus, only those two types of mRNA encode the complete sequence of Substance P. Exon 4 is missing in γPPT-A mRNA, thus Neuropeptide K cannot be transcribed from this mRNA. The production of Substance P by all 4 splice variants suggests that when the PPT-A gene is expressed, also Substance P is produced. The expression of αPPT-A mRNA occurs predominantly in the brain, while, βPPT-A and γPPT-A mRNA molecules are predominantly expressed in peripheral tissue.

The PTK-A fragment 1-37 plays a central role in this invention and is called A-peptide herein.

DETAILED DESCRIPTION OF THE INVENTION

Substance P and other tachykinins can be detected in different body fluids, tissues and other biomaterials.

The short half-life of tachykinins in blood, however, so far has hindered the use of tachykinins, especially of Substance P, in routine diagnostics. Due to the short half-life of tachykinins, it is not possible in clinical routine to take the samples, obtain the plasma, transport the sample into the laboratory and do the diagnostics in the laboratory including the required tests before tachykinin degradation reach a critical level.

Thus due to the low in vivo stability of tachykinins like Substance P, the use as a biomarker is extremely limited even under optimized sample logistics, as the influence of the degradation of the peptides extremely dilutes the influence of bio-synthesis and tachykinin release.

The object of the invention was to overcome the disadvantageous half-life of the tachykinins and to develop a method, use and a kit for the detection and determination of tachykinin in body fluids, tissues and other biomaterials.

This object has been achieved by the surprising finding that protachykinin can be used as a tool for the determination of tachykinins in body fluids, tissues and other biomaterials, particularly Substance P. This presence of the protachykinins correlates with the presence of the mature tachykinins like Substance P in the different body fluids/tissues or biomaterials.

Furthermore, the stability of protachykinin, its splice variants, fragments and/or combinations thereof ex vivo is surprisingly high and renders the protachykinins fully suitable for routine purposes.

The same applies for the in vivo half-life of protachykinin that is significantly higher than those of Substance P, Neurokinin A and Neuropeptide K, which renders them suitable to be used in the detection of Substance P/protachykinin concentration and release rate.

This linkage between the protachykinins of the present invention and the mature peptides makes them suitable as diagnostic tools for all diseases and/or disorders, where the mature proteins like Substance P, Neurokinin A, Neuropeptide K and Neuropeptide γ play a role.

Protachykinin can therefore be used for diagnostics for a variety of diseases comprising diseases of the central nervous system, comprising Alzheimer's disease, Parkinson's disease, depression and/or conditions of pain, local, systemic, chronic, inflammatory diseases, infectious diseases comprising bacterial and viral infections, sepsis, Crohn's disease, colitis ulcerosa, meningitis, sickle cell anemia, ischemia, amyotrophic lateral sclerosis, arthritis, rheumatoid arthritis, bronchitis, hyperalgesia, asthma, intoxication comprising bacterial intoxication, immunological disorders, cranio-cerebral trauma, tumors, stroke, stress, atopis dermatitis, HIV, Huntington's disease, burns, fibromyalgy, schizophrenia, Hirschsprung's disease, allergies, familial dysautononmia (Riley Day syndrome), hematopoietic disorders, gliomas comprising glioblastomas and astrocytomas.

Furthermore, the present invention in one embodiment relates to the use of the above-mentioned protachykinins for early diagnosis, diagnosis of the degree of severity of the disease, course control and prognosis for the above-mentioned diseases/disorders and/or comprising those diseases/disorders where the mature protein plays a role.

Clinical data may additionally be taken into consideration to support the determination of the disease/disorder.

The present invention in a further embodiment relates to the production of protachykinin and fragments. It is further possible to use amino acid sequences showing at least 75% homology, preferred at least 80% homology, more preferred at least 90% homology to protachykinin according to the present invention.

The synthetic peptides in accordance with the present invention were used to produce antigens and injected into animals to raise antibodies against the protachykinin. Different methods can be used to achieve this object known by the person skilled in the art. In a preferred embodiment hemocyanin from *Limulus polyphemus* was used for the immunization of rabbits.

In a preferred embodiment of the invention 10 amino acid sequences (sequence IDs 1-10) of protachykinins were synthesized, more preferred four different peptide sequences (PSPI to PSP4, see FIG. 4a) of protachykinin A were synthesized: The peptides PSPI and PSP2 comprise the sequence for the A-peptide. PSP3 contains the first part of the sequence of active Neuropeptide K (NPK) and PSP4 also comprises parts of the sequence of NPK as well as Neuropeptide γ (NPγ) and the complete sequence of Neurokinin A (NKA). An amino-terminal cystein residue was added to each peptide. The peptides were conjugated to a hemocyanin from *Limulus polyphemus* and antibodies were produced to PSPI-PSP4 in rabbits according to known methods.

Antibodies were purified according to known methods, in a preferred embodiment of the invention, this was achieved preferably by ligand specific affinity chromatography by coupling the peptides via the amino terminal cystein residue to SulfoLink-Gel of Pierce (Boston, USA) according to the methods of Pierce.

In a preferred embodiment the antibodies were tagged with a marker to enable detection. The marker used is preferably a luminescent marker and in a yet more preferred embodiment, the antibodies against PSPI were tagged with a luminescent marker.

The invention in a yet further embodiment involves the use of the generated antibodies for detection of protachykinin in body fluids, tissues or other biomaterials, as well as a kit containing a certain quantity of such an antibody specific to detect protachykinin.

Methods for the detection of binding of the antibody to the respective molecule are also known by the person skilled in the art. In one embodiment of the invention, the binding of the antibody to the target (which contains protachykinin) is detected by luminescence.

A preferred embodiment of the invention discloses the use of antibodies generated against PSPI to PSP4: Different antibody combinations (Table 1) were used for the detection of protachykinin in control individuals, in patients with Alzheimer's disease and in sepsis patients in plasma and liquor. The protachykinin-fragments detected by the antibodies are shown in Table 1.

The invention further permits the determination of the presence and stability of protachykinin in body fluids, tissue and other biomaterials and the difference in protachykinin concentration in healthy controls and patients of various diseases.

In one embodiment the invention is based on and uses the discovered long term stability of protachykinin ex vivo in plasma (FIG. 2). In plasma protachykinin surprisingly has a half-life of more than 24 h. As less peptidases are present in CSF, protachykinin is expected to be even more stable in CSF (cerebro-spinal fluid) than in plasma.

A further embodiment of the invention discloses the in vivo half-life of PTK/A-peptide surprisingly being more than 60 mins. (FIG. 3), as compared to the halflives of Substance P (1-2 mins), Neurokinin A (<2 mins.) and Neuropeptide K (6 mins.).

Thus protachykinin is by far more suitable for diagnostic purposes than the mature proteins like Substance P.

The invention further uses the correlation of protachykinin and mature tachykinins like Substance P in the state of disease/disorder in body fluids, tissues or other biomaterials, blood and liquor in particular.

In one embodiment of the invention the level of immune reactivity of protachykinin with the three antibody combinations of table 1 of control plasma, sepsis/plasma, Alzheimer's disease/plasma and liquor of healthy control individuals is shown (see also example 4). An increase in protachykinin level in plasma is observed in diseased patients (antibody combination I, black column) as compared to plasma of healthy control individuals (FIG. 5). Antibody combination I detects the A-peptide (fragment 1-37) and A-peptide containing peptides, that is present in all four splice variants (αPPT-A, (βPPT-A, γPPT-A and δPPT-A). Antibody combination II detects only splice variants αPPT-A and βPPT-A and combination III only, βPPT-A and γPPT-A. Using antibody combination I, the A-peptide concentration in plasma of sepsis and Alzheimer's patients is significantly increased, 2-fold and 12-fold, respectively (see FIG. 5). Antibody combinations II and III also show a 2.5-fold increase of protachykinin level in the plasma of Alzheimer's patients and about 2.8-fold increase in plasma of sepsis patients. In liquor of healthy controls (far right columns of FIG. 5), antibody combination I shows a signal, antibody combinations II and ill do not show a significant signal.

These results are consistent with those of Substance P in Alzheimer's patients, sepsis, stroke, cerebral ischemia, infection, symptoms of pain, lung disorders and tumors.

The invention discloses the level of protachykinin in body fluids, tissue and other biomaterials of healthy control individuals and diseased persons.

In a preferred embodiment the invention discloses the distribution of A-peptide concentrations in plasma of healthy individuals (FIG. 7). 90% show an immune reactivity below 35 pg/ml, the median was 13.3 pg/ml.

The invention further discloses a significant change of protachykinin concentration in body fluids, tissues and other biomaterials in disease or disorder, preferentially comprising diseases of the central nervous system, comprising Alzheimer's disease, Parkinson's disease, depression and/or conditions of pain, local, systemic, chronic, inflammatory diseases, infectious diseases comprising bacterial and viral infections, meningitis, sepsis, Crohn's disease, colitis ulcerosa, sickle cell anemia, ischemia, amyotrophic lateral sclerosis, arthritis comprising rheumatoid arthritis, bronchitis, hyperalgesia, asthma, intoxication comprising bacterial intoxication, immunological disorders, poly/-trauma comprising cranio-cerebral trauma, tumors, stroke, stress, atopis dermatitis, HIV, Huntington's disease, burns, fibromyalgy, schizophrenia, Hirschsprung's disease, allergies, familial dysautonomia (Riley Day syndrome), hematopoietic disorders, gliomas comprising glioblastomas and astrocytomas, disorders of the blood brain barrier.

A preferred embodiment of the invention is based on the surprising finding of a significant 2-fold increase in A-peptide concentration in Alzheimer's patients as compared to age-matched healthy control individuals, as is consistent with the results of Substance P. The corresponding embodiment of the invention resides in a diagnostic method and kit for testing body samples, in particular blood, plasma or liquor with an antibody specific for protachykinin, its precursors or fragments, in particular A-peptide.

A further preferred embodiment of the invention discloses a significant increase of A-peptide containing immune reactivity in pneumonia, local infection (abscesses), sepsis, trauma and polytrauma patients and diverse tumors (FIG. 10), intoxication, systemic inflammation (FIG. 11) and functioning of the blood brain barrier (FIG. 9). The liquor of healthy individuals contains 150 to 450 μg of protein per ml, 83% of the proteins are synthesized in the serum, and only 17% in the brain. Prostaglandin-D-synthetase shows the highest quotient liquor to serum of 33 so far determined. A preferred embodiment surprisingly shows that the A-peptide immune reactivity has a quotient of serum to liquor of more than 80 and thus surprisingly is significantly higher than of other proteins. As the concentration of A-peptide is higher in liquor than in plasma, an increase of A-peptide in plasma indicates the damage or loss of function of the blood brain barrier: the liquor diffuses into plasma leading to an increase in protachykinin concentration in plasma. The determination of A-peptide or A-peptide immune reactivity is thus a potent plasma marker for the functioning of the blood brain barrier.

Thus the invention also provides a diagnosis method and kit for the above mentioned diseases/disorders, both having or using an antibody for protachykinin.

The invention discloses the use of protachykinin and J or its antibodies for detection, course control and prognosis of disease.

A preferred embodiment of the invention determines the A-peptide concentration in blood during the course of diseases like meningitis, cranio-cerebral trauma and stroke (until reconvalescence or exitus) in FIG. 9. In a diseased state patients show a significantly increased level of A-peptide (above 35 pg/ml) that decreases during reconvalescence, but remains constantly significantly increased until exitus of patient's having a stroke.

DESCRIPTION OF THE FIGURES

FIG. 4 *c* shows splice variants of γ-PPT-A (AS 1-95, Sequence ID 5).

FIG. 4 *d* shows splice variants of δ-PPT-A (AS 1-77, Sequence ID 8).

EXAMPLE 1

Production of Antibodies (a) Immunogen

Figure 1:
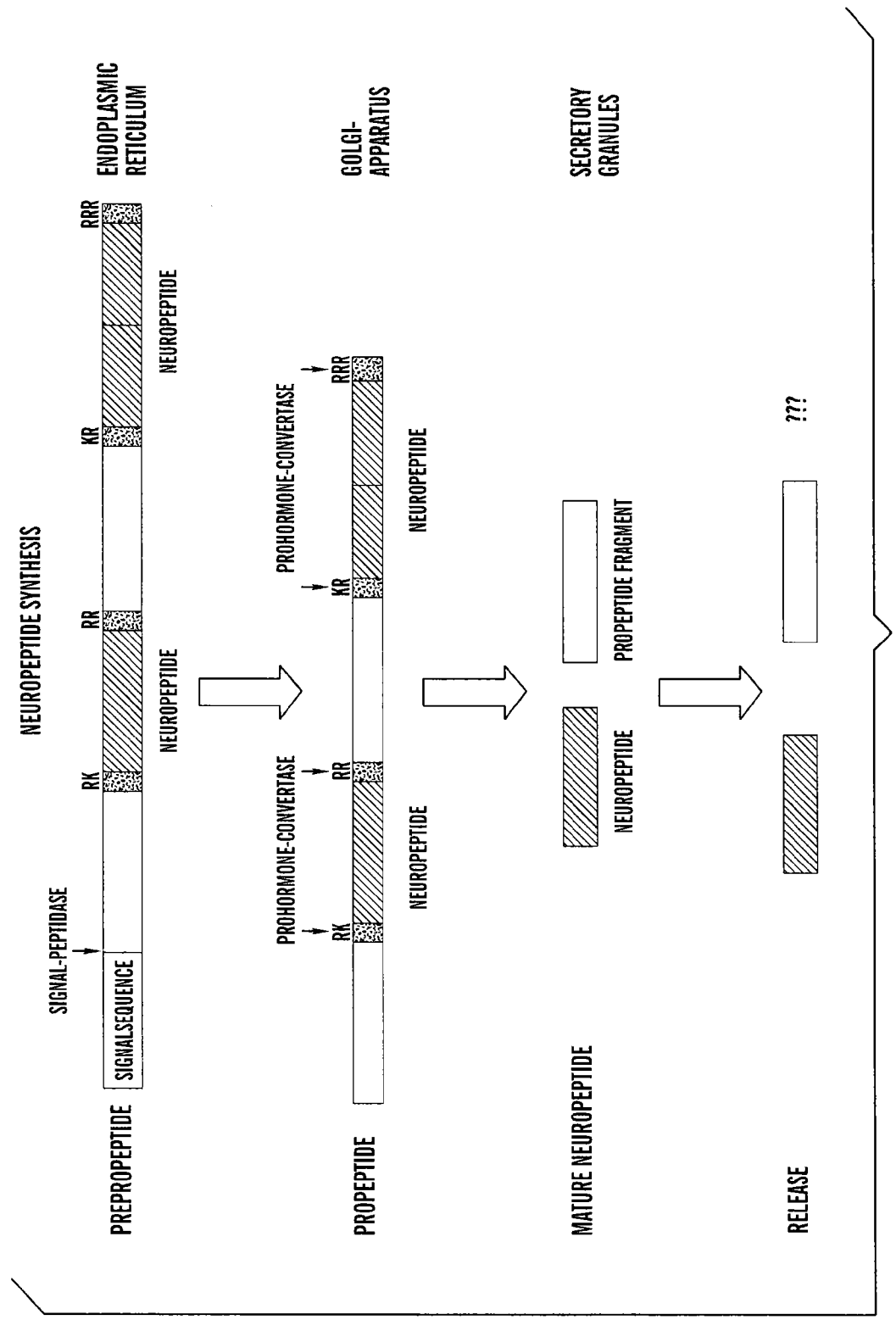
FIG. 1 shows the biosynthesis of neuropeptides in vivo.
Figure 2:
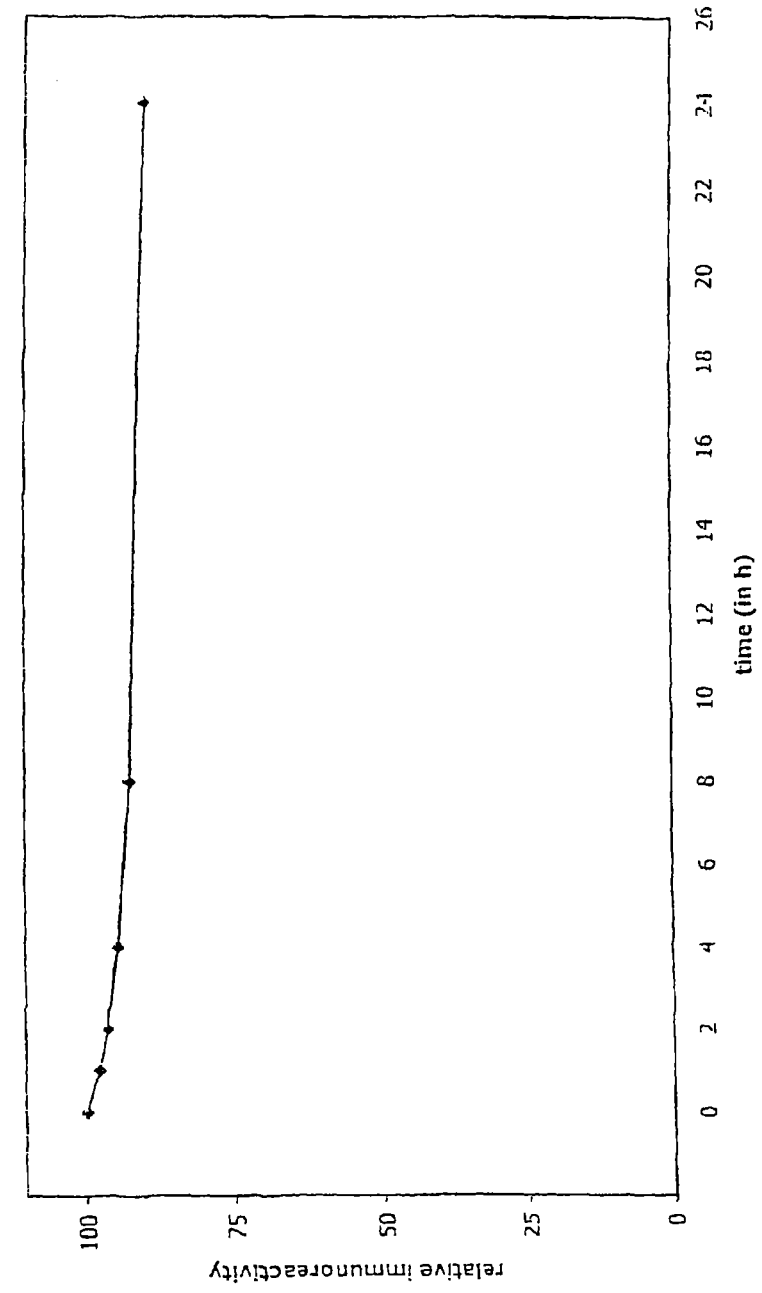
FIG. 2 shows the stability of protachykinin-fragments ex vivo (EDTA-plasma). The half-life of protachykinin at room temperature is more than 24 h.
Figure 3:
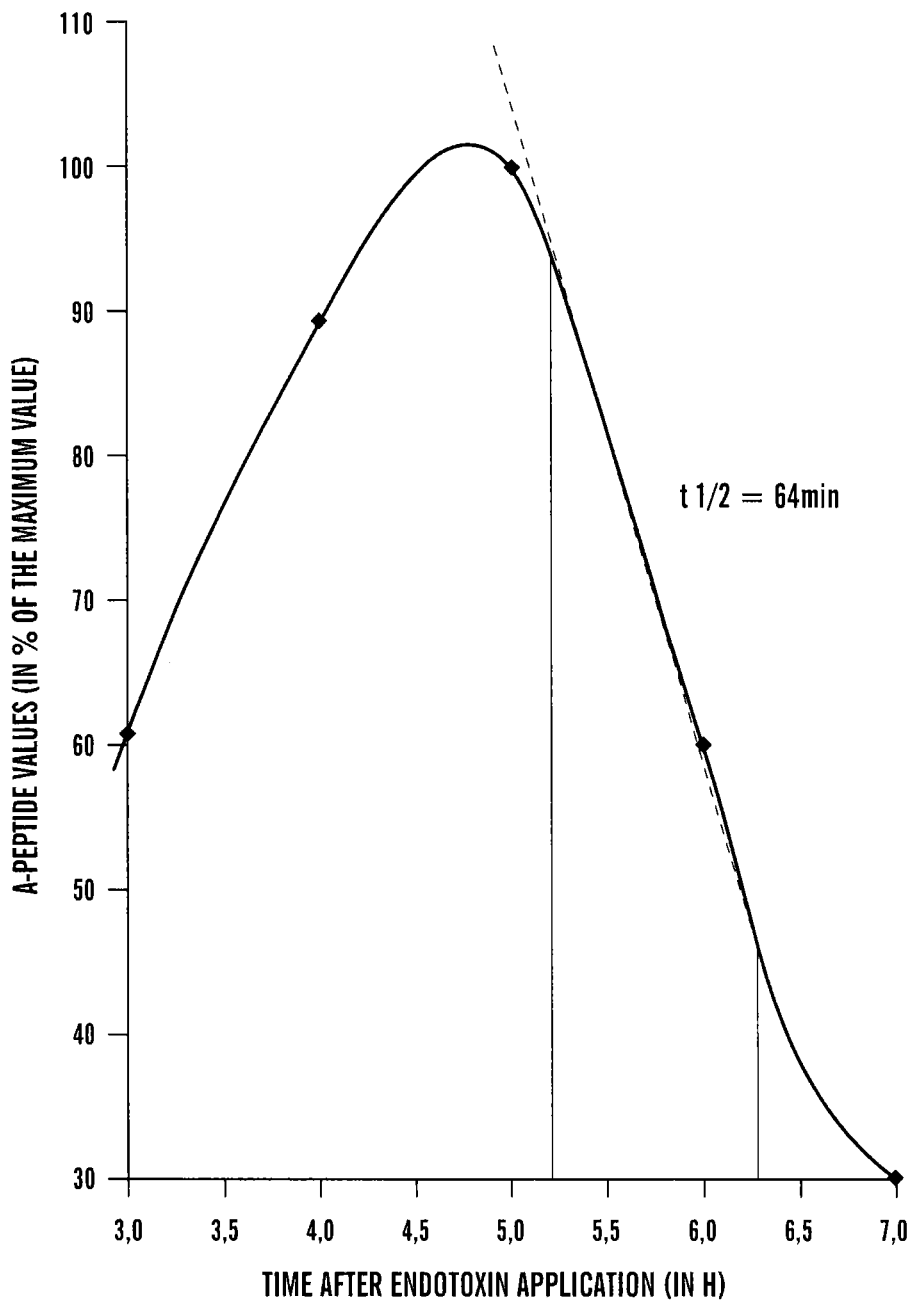
FIG. 3 shows the determination of protachykinin-fragments in vivo after application of endotoxin. The half-life of PTK/A-peptide is more than 60 mins. in vivo.

Four different peptide sequences (PSPI to PSP4), see FIG. 1) of protachykinin A were selected and synthesized by Jerini (Berlin, Germany). The peptides PSP 1 and 2 comprise the sequence of the A-peptide. PSP3 comprises the first part of the first sequence of the active neuropeptides K (NPK) and PSP4 also shows parts of the sequence of NPK as well as of neuropeptide γ (NP γ) and the complete sequence of neurokinin A (NKA). Each peptide was provided with an amino-terminal cystein residue (Cys0).

(b) Antibodies

For the immunization the respective peptide was conjugated with the haemo-cyanine from *Limulus polyphemus* by BioGenes (Berlin, Germany) antibodies were produced against the PTK-peptide-conjugate PSPI to PSP4 in rabbits.

EXAMPLE 2

Purification of the Antibodies

The antibodies were purified by a ligand specific affinity purification. For that step the Cys(0)-peptides PSPI to PSP4 were linked to SulfoLink-Gel supplied by Pierce (Boston, USA). The binding occurred according to the protocol of the provider.

In summary, polycarbonate columns (15 mm×80 mm) were filled with 5 ml affinity matrix. After equilibration of the columns with PBS (phosphate buffered saline) (136 mM NaCl, 1.5 mM $KH_2PO_4$, 20.4 mM $Na_2HPO_4*2H_2O$, 2.7 mM KCl, pH 7.2) 5 mg of the respective peptide were dissolved in PBS applied to the closed columns and the gel material was homogenized by gentle rotation. After 15 min of incubation at room temperature and settling of the gel material, the columns were washed 5 times with 3 ml PBS. To saturate free binding positions 5 ml of a 50 mM L-cysteine solution were added to the material of the column and the gel material after homogenization was again incubated for 15 min at room temperature. After settling of the gel material each column was washed 6 times with 5 ml of a 1 M NaCl solution followed by washing with PBS.

The gel material was mixed with 25 ml of the respective pools of antiserum and incubated over night at room temperature by gentle rotation. The serum-gel mixture was added to polycarbonate columns and surplus serum was removed. The columns were then washed with 250 ml PBS to remove unbound serum proteins. The desorption of unbound antibodies was done by elution of the column with 50 mM citric acid (pH 2.2). The eluate was captured in fractions of 1 ml. The protein concentration of each fraction was determined using the BCA-protein assay kit of Perbio (Bonn, Germany) and the fractions with a protein content>1 mg/ml were combined. The affinity purified antibodies were rebuffered in PBS via dialysis. The protein content was determined again and the antibodies were stored at 4° C.

EXAMPLE 3

Immobilization/Tagging of the Antibodies

The purified antibodies against the peptide PSP2, 3 and 4 were immobilized on polystyrol tubes (startubes, 12 mm×75 mm, Greiner, Germany). For that procedure the antibody solutions were diluted to a protein concentration of 6.7 µg/ml with PBS and 300 µl per tube were pipetted (corresponds to 2 µg antibody per tube). These were incubated for 20 hours at room temperature and then washed 3 times with 4 ml PBS, respectively. Until further use the tubes were stored at 4° C. The antibody against PSP1 (1 mg/ml in PBS) was tagged with the luminescent marker Acridiniumester-N-Hydroxy-Succinimid (1 mg/ml in acetonitrile, InVent, Hennigsdorf, Germany). For the tagging procedure 200 µl of antibody were mixed with 4 µl acridinium ester, incubated for 20 minutes and free acridinium ester bonds were saturated by adding 40 µl of a 50 mM glycine solution. The tagging preparation was separated from free acridinium ester by HPLC in a BioSil 400-gel filtration-column (BioRad, Munich, Germany). PBS was used as a solvent.

EXAMPLE 4

Determination of the Protachykinin Immune Reactivity

The protachykinin immune reactivity was determined in plasma using three different combinations of antibodies of 5 controls each, sepsis and Alzheimer patients as well as in the liquor of 5 non-demented control patients. 100 µl samples were pipetted per coated tube and 12.5 ng of the tagged antibodies (in 200 µl PBS buffer, 10 mM EDTA) were added to each tube. The tubes were incubated at 4° C. for 20 hours. Subsequently, unbound tracer antibody was removed by washing 5 times with 1 ml PBS each. Tagged antibody bound to the tube was quantified by detecting the luminescence in a luminometer (Berthold LB 952T/16).

Figure 4A:
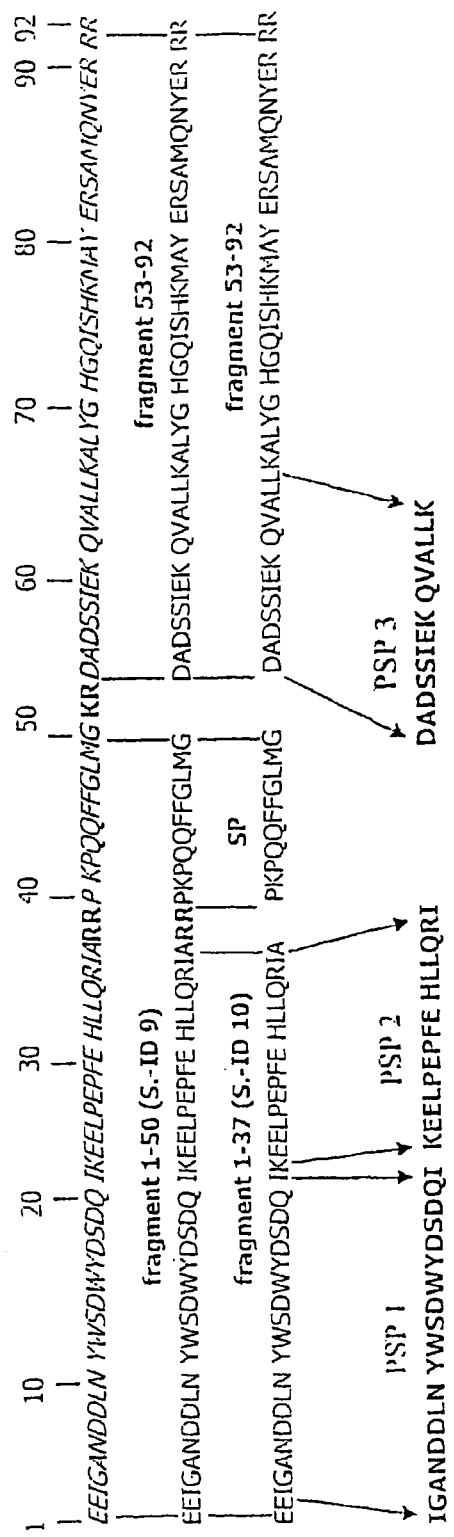
FIG. 4 a shows the splice variants of α-PPT-A (AS 1-92, Sequence ID 1).
FIG. 4b shows splice variants of β-PPT-A (AS 1-110, Sequence ID 2).
Figure 4B:
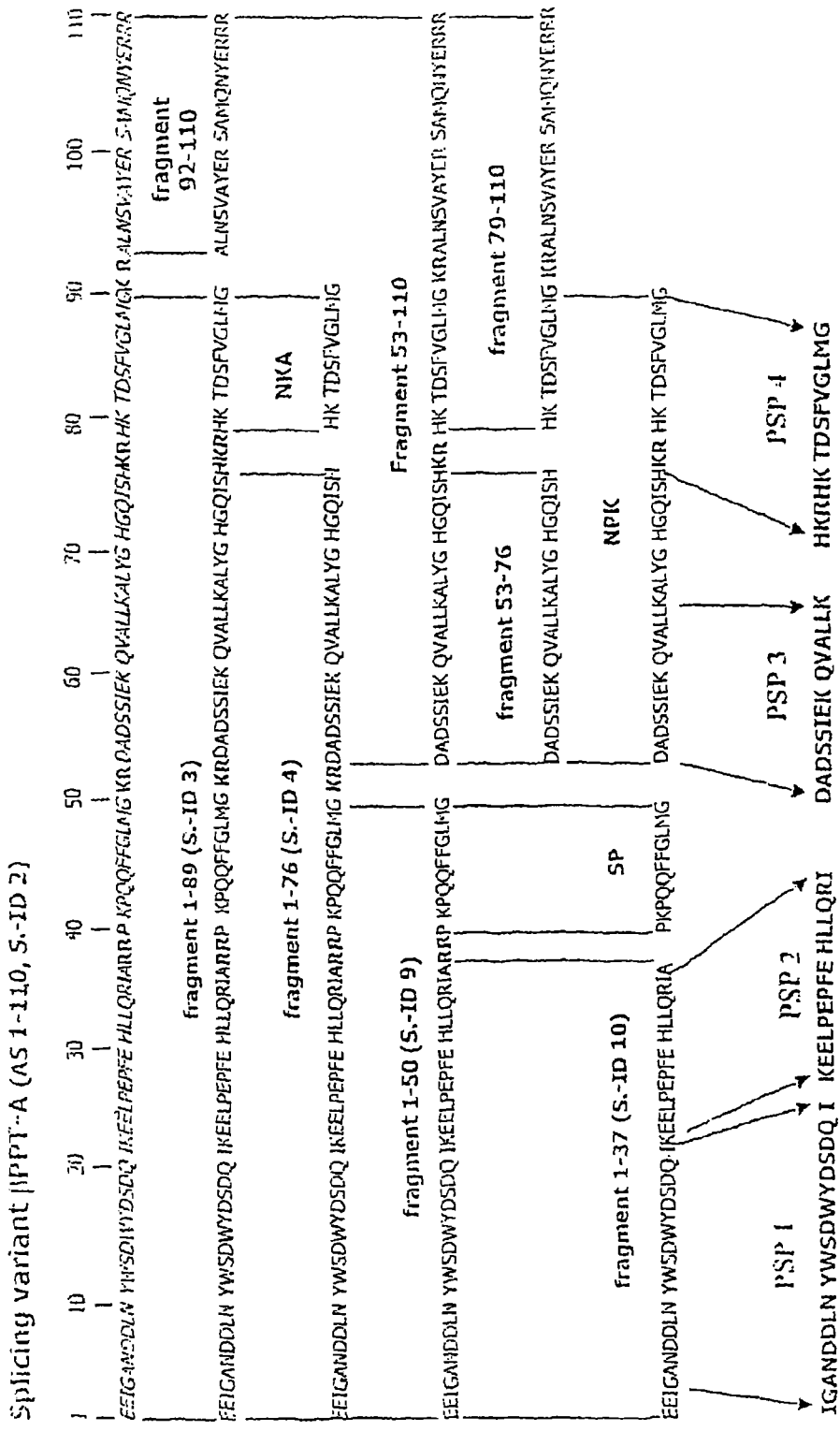
Figure 4C:
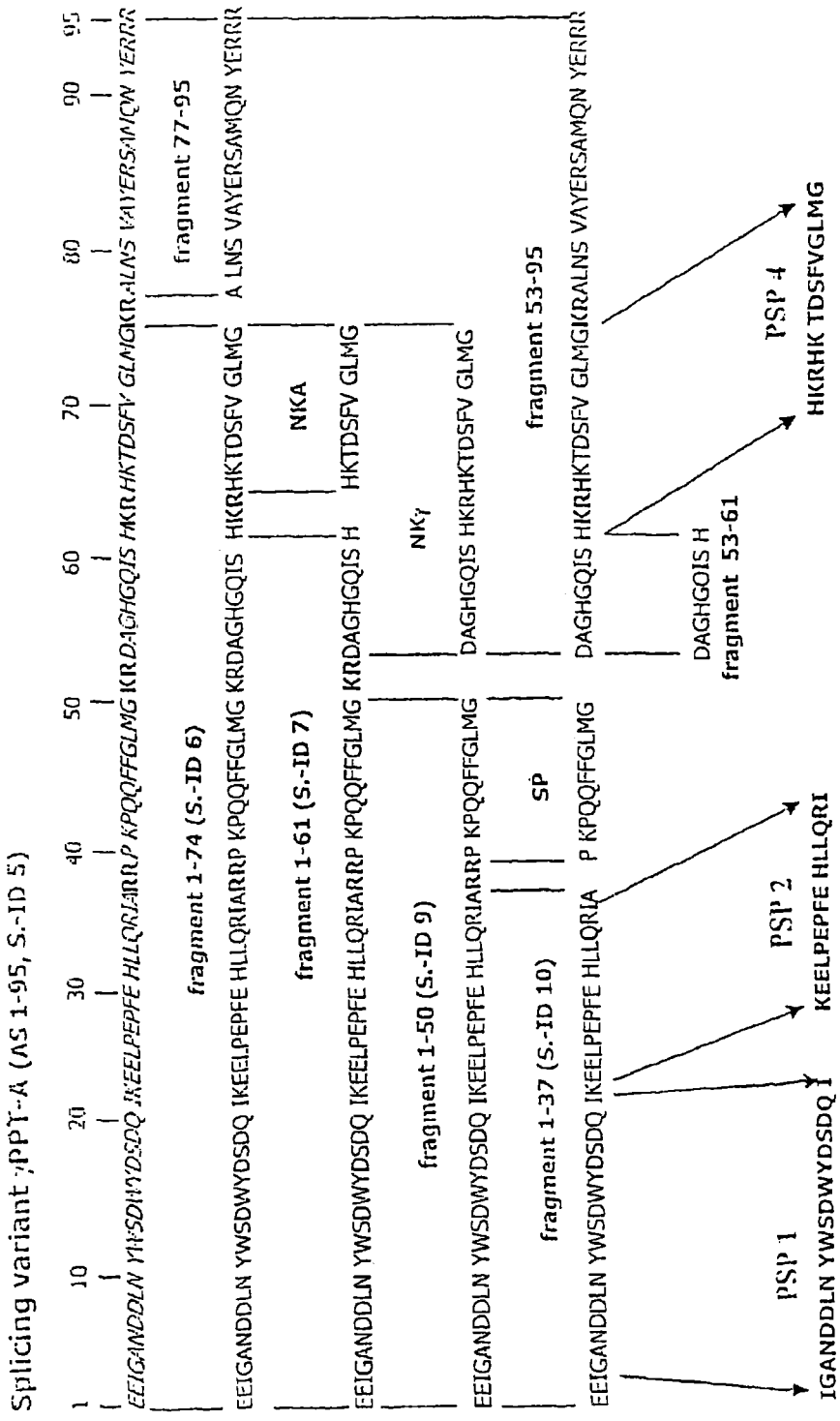
Figure 4D:
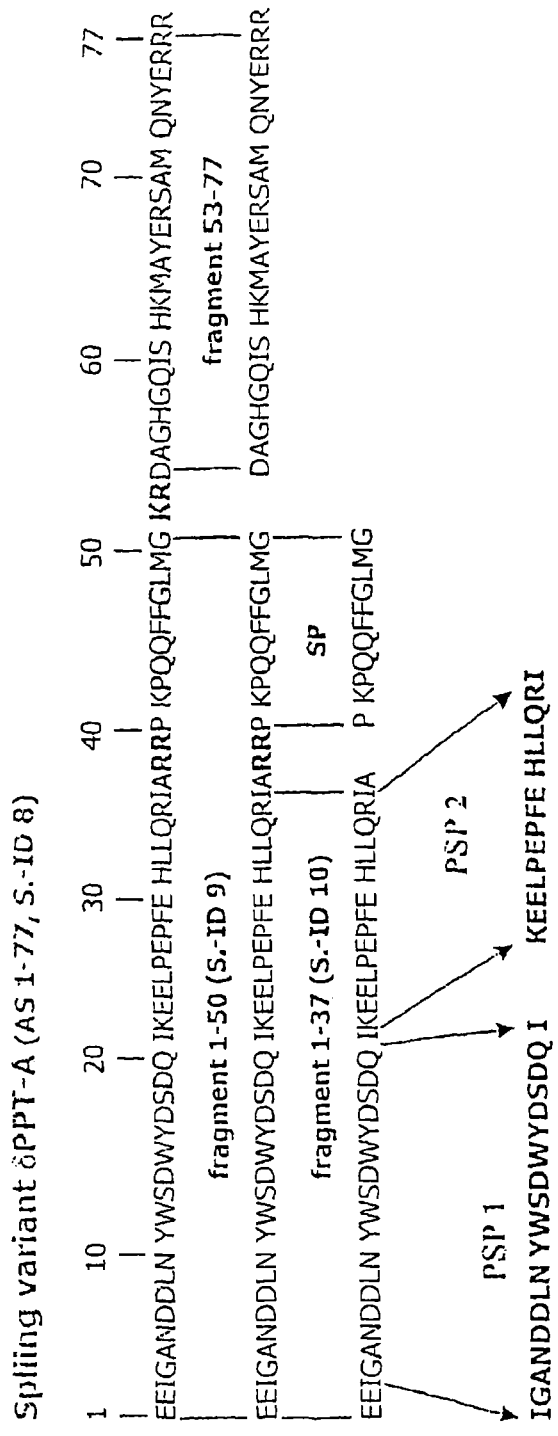
Figure 5:
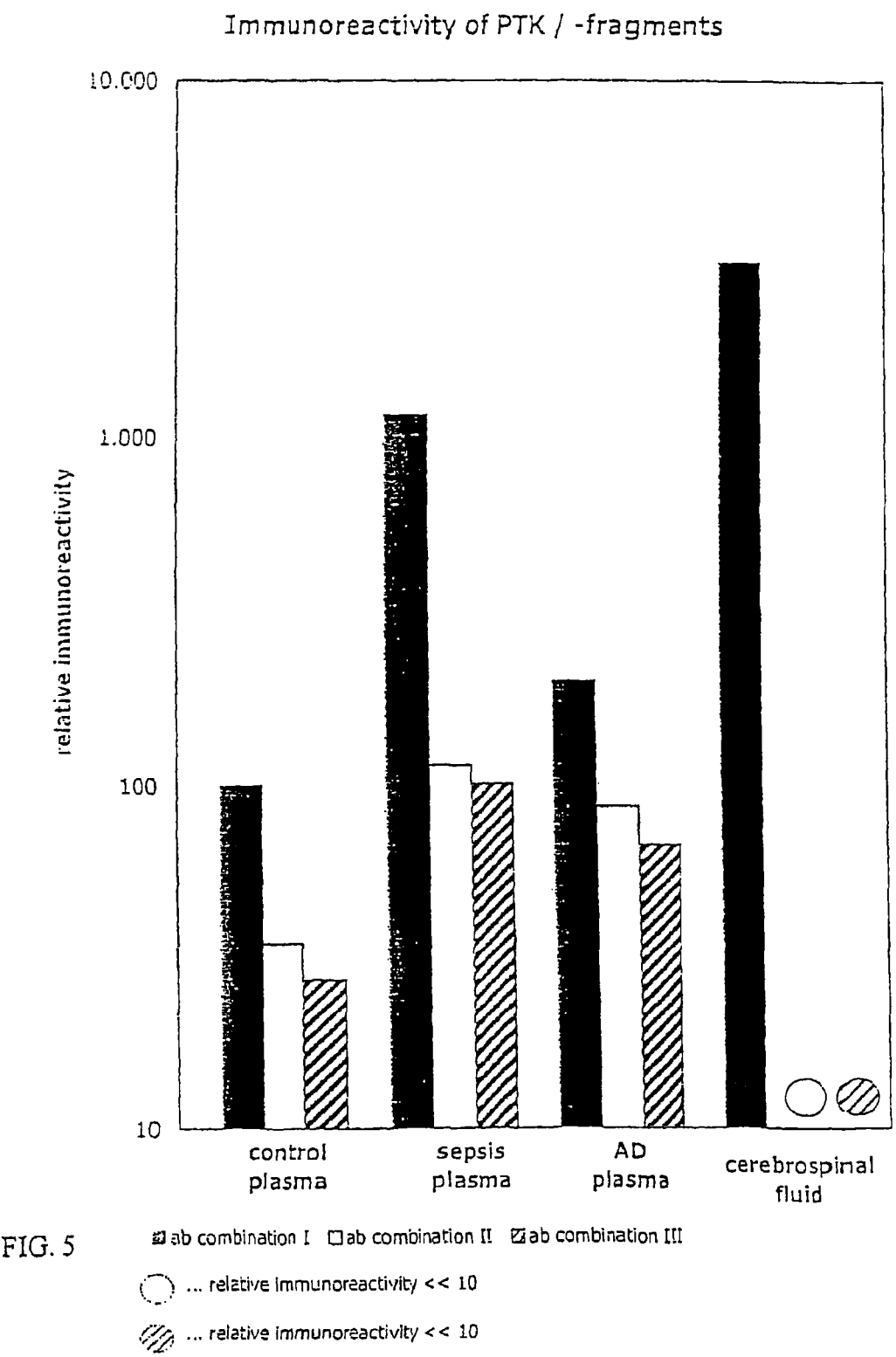
FIG. 5 shows immune reactivity of antibody combinations I-III in plasma of healthy control individuals, sepsis, Alzheimer's patients and liquor of healthy controls.

The PTK fragments detected by the different combinations of antibodies (FIG. 4*a*) are shown in the Table below and in FIG. 4*b*. The measured relative immune reactivities with 3 antibody combinations are shown in FIG. 5. Antibody combination I detects the A-peptide (Fragment 1-37) that is comprised in all 4 splicing variants (αPPT-A, βPPT-A, γPPT-A and δPPT-A). Antibody combination II detects only splicing variants αPPT-A and βPPT-A and combination III only βPPT-A and γPPT-A.

In the plasma of controls, sepsis and Alzheimer patients protachykinin sequences comprising all three antibody combinations could be detected. The average value of the control data for the detection of α/β/γ/δ the antibody combination I was calibrated to 100% for a better comparison between the results and the average values of the remaining data were referred to that (see Table 1). It is shown that the A-peptide and the PTK-fragments comprising all the sequences show by far the highest concentration in liquor and show a 30-fold higher signal than in the plasma of healthy controls. The immune reactivity of A-peptide is clearly increased also in plasma of sepsis patients. Here, the signal is about 12 times higher than in the plasma of control individuals. Alzheimer's patients show a signal increased by factor 2.

The splice variants α/β and β/γ in combination with the antibody combinations II and III do not show a detectable signal in liquor. This indicates that PTK is present as the fully processed protein. In plasma, however, splice variants α/β and β/γ with the combinations II and III could be detected, these, however, were running below the signals for α/β/γ/δ (antibody combination 1).

The detection of PTK-fragments by the antibody combination I show a quotient of 11.6 and 2.0 in sepsis and Alzheimer samples, respectively, with reference to the control samples. The quotient of the sepsis samples of the antibody combinations II and III is considerably lower than 11.6 of the antibody combination 1. Thus, this combination is a better method for the differentiation of healthy controls, at least for sepsis patients. (The choice of antibody combinations does not seem to be relevant for the differentiation of controls and Alzheimer patients, as the quotient for the Alzheimer samples in combination with all three antibody combinations is in the range of 2.)

TABLE 1

Measurement of the relative immune reactivity of PTK/-fragments in combination with different antibody combinations

| Antibody combination | I (PSP2/PSP1) | II (PSP3/PSP1) | III (PSP4/PSP1) |
|---|---|---|---|
| Detected splice variants | α/β/γ/δ | α/β | β/γ |
| Detectable PTK-fragments | AS 1-37 (α/β/γ/δ)<br>AS 1-50 (α/β/γ/δ)<br>AS 1-92 (α)<br>AS 1-76 (β)<br>AS 1-89 (β)<br>AS 1-110 (β)<br>AS 1-61(γ)<br>AS 1-74(γ)<br>AS 1-95(γ)<br>AS 1-77(δ) | AS 1-92(α)<br>AS 1-76 (β)<br>AS 1-89 (β)<br>AS 1-110 (β) | AS 1-89 (β)<br>AS 1-110 (β)<br>AS 1-74(γ)<br>AS 1-95(γ) |

| Sample | rel. IR | quotient | rel. IR | quotient | rel. IR | quotient |
|---|---|---|---|---|---|---|
| Control sample | 100 | 1.0 | 45.6 | 1.0 | 36.4 | 1.0 |
| Sepsis plasma | 1160 | 11.6 | 114 | 2.5 | 101 | 2.8 |
| Alzheimer disease plasma | 200 | 2.0 | 86.5 | 1.8 | 67 | 1.8 |
| Liquor | 3096 | 30.96 | 6 | 0.1 | 5.5 | 0.15 | rel. IR relative immune reactivity (values in % in response to the control plasma value of antibody combination I which was calibrated to 100%). All values are average values (n = 5). Quotient ratio of the respective value of the patient (in %) and the corresponding control value (in %) of the respective antibody combination.

EXAMPLE 5

Immunoassay for the Quantitative Determination of A-Peptide

1. Components

Tubes coated with PSP2-antibody and PSP1-antibody tagged with a luminescent marker were used in the immunoassay. The production of these components is described in example 3.

2. Procedure

100 µl of sample were pipetted in each tube coated with antibody and 12.5 ng of the tagged antibody (in 200 µl PBS buffer, 10 mM EDTA) were added. The tubes were incubated for 20 hours at 4° C. and subsequently tracer antibody was removed by washing 5 times with 1 ml PBS. Tagged antibody bound to the tube was quantified by measuring the luminescence in a luminometer (Berthold LB 952T/16).

3. Calibration

Figure 6:
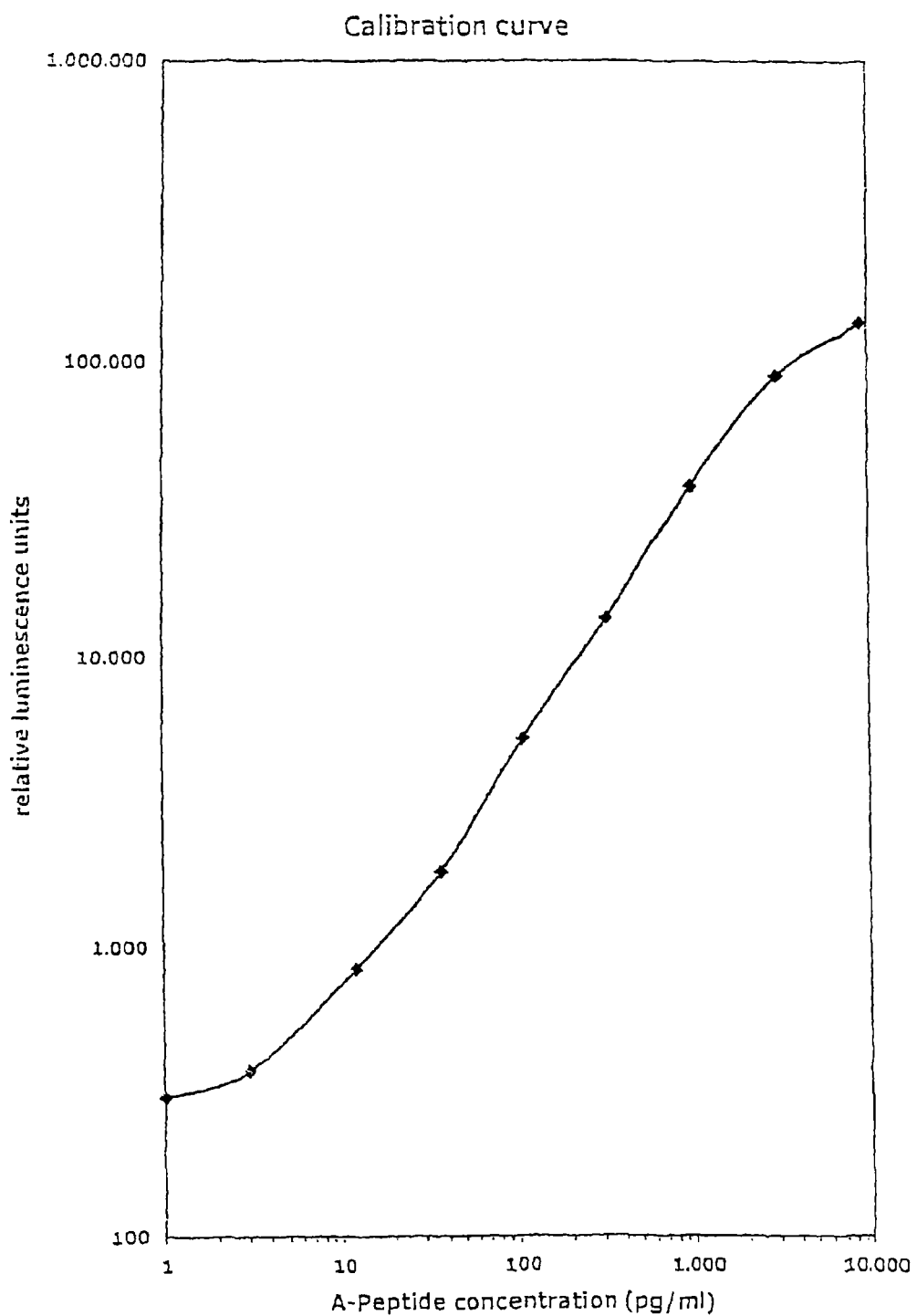
FIG. 6 shows standard curve of luminescence (relative luminescence units) in dependence of A-peptide concentrations (pg/ml).

To be able to determine the concentrations and the immune reactivities, of A-peptide, the peptide was synthesized by Jerini (Berlin, Germany). The weighed out peptide was used as a calibrator for the immunoassay. In FIG. 6 the standard graph of A-peptide is shown. The analytical sensitivity of A-peptide assays is about 4 pg/ml.

EXAMPLE 6

A-Peptide Concentratiolls in Plasma of Supposedly Healthy Individuals (Controls)

Figure 7:
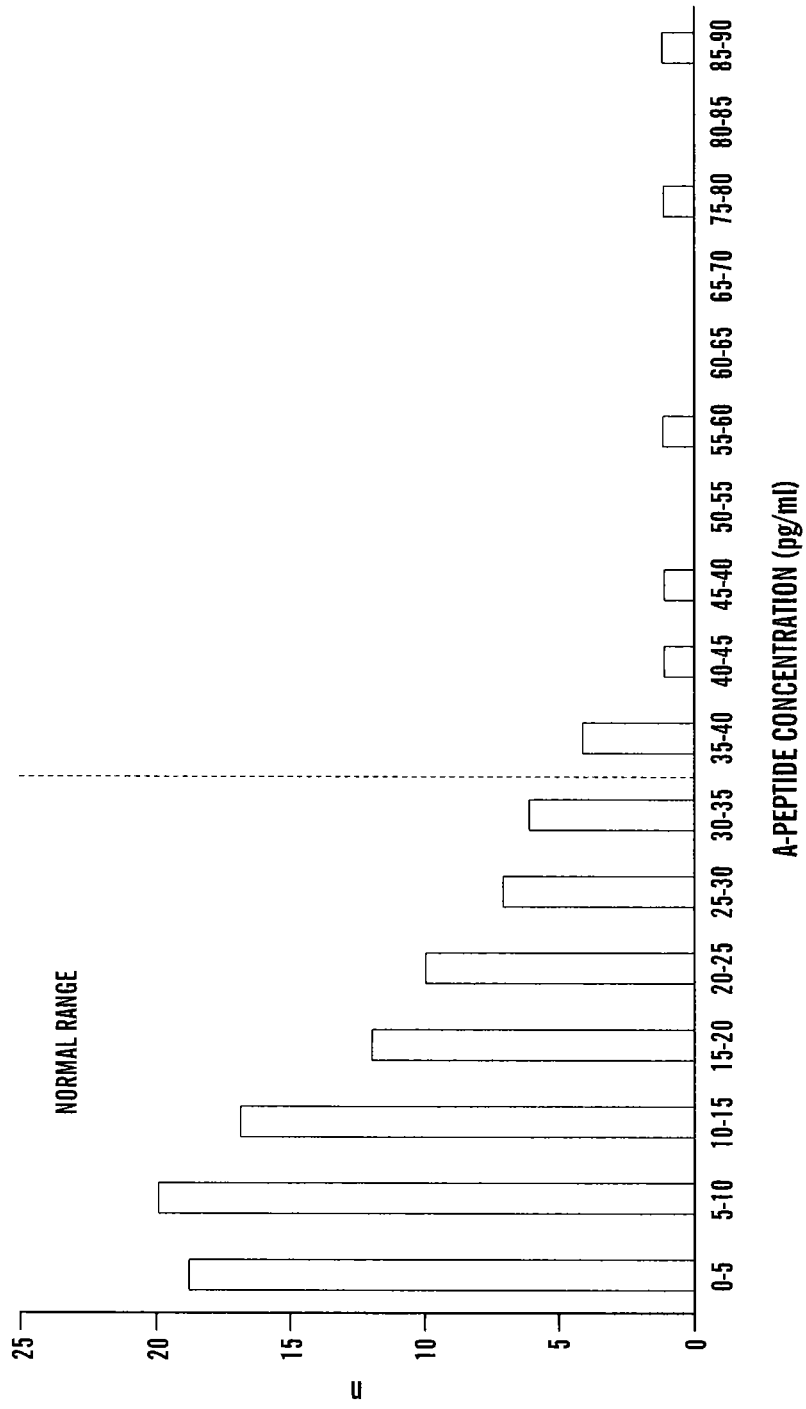
FIG. 7 shows the distribution curve of A-peptide concentrations in plasma of healthy control individuals (pg/ml).

The distribution graph of the A-peptide concentration in plasma of healthy individuals was shown in FIG. 7. 90% of the 100 control samples show an A-peptide immune reactivity below 35 pg/ml. The median was 13.3 pg/ml.

EXAMPLE 7

A-Peptide Content in Alzheimer's Disease

Figure 8:
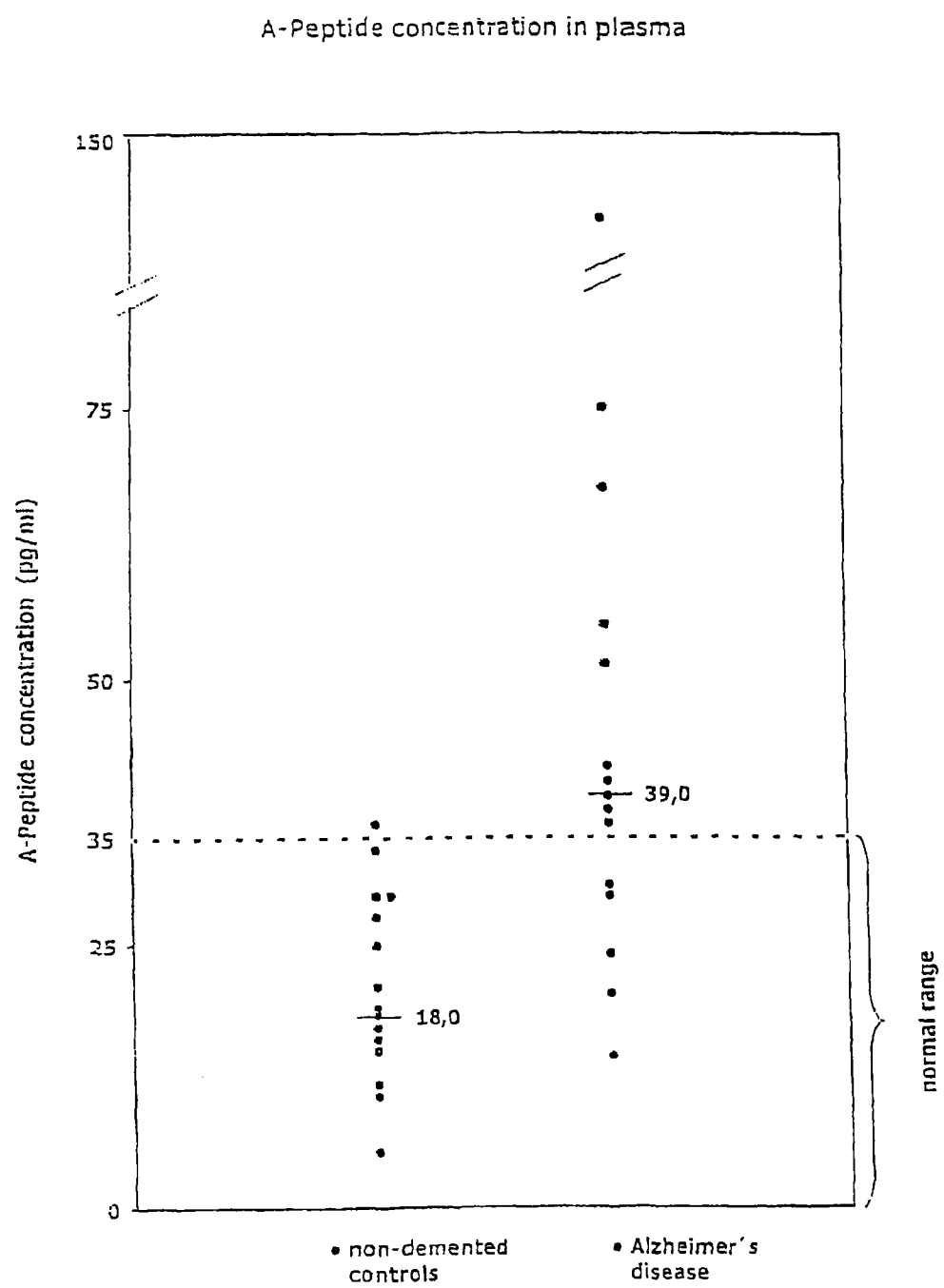
FIG. 8 shows the A-peptide concentration in plasma of Alzheimer's patients and non-demented age-matched controls.

The A-peptide immune reactivity in plasma of patients suffering from Alzheimer's disease and non-demented age-matched controls differ significantly (FIG. 8). The median of the controls in this case is 18.0 pg/ml, the median of Alzheimer's patients is increased by factor 2, i.e. it is 39.0 pg/ml.

EXAMPLE 8

A-Peptide Concentrations in Cerebrospinal Fluid (CFS)

The A-peptide concentration in liquor of control samples (n=30) was determined and a median of 1085 pg/ml was determined. The CSF-median is increased significantly by a factor of about 80 above the median of plasma of healthy control individuals.

EXAMPLE 9

A-Peptide Concentration in Impairments of the Blood-Brain Barrier

Figure 9:
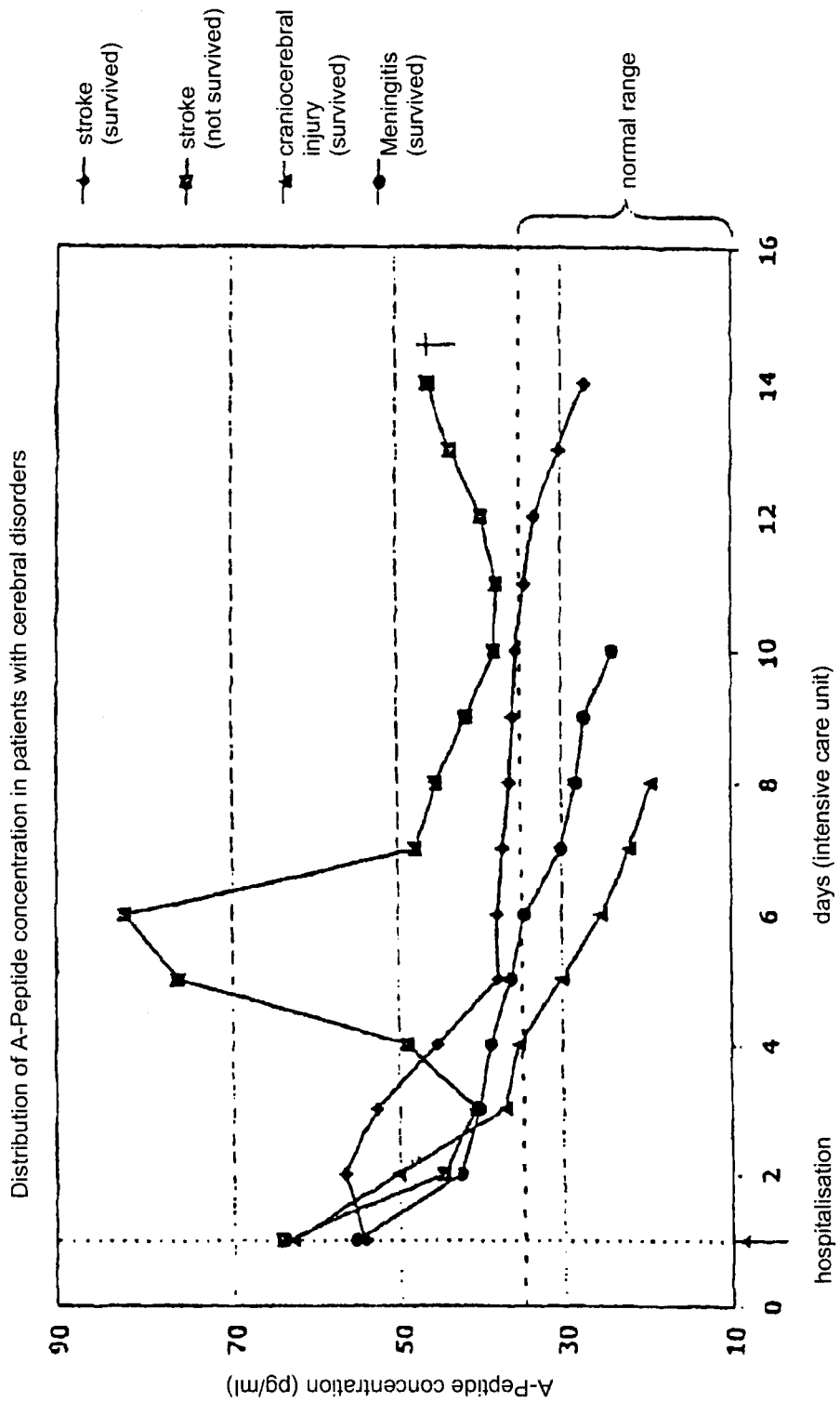
FIG. 9 shows the course of patients with cerebral disorders, showing the concentration of A-peptide in stroke (reconvalescence and exitus), meningitis and cranio-cerebral trauma during course of disease from admission to hospital to day 14 or exitus.

The A-peptide content in the circulation in the course of disease of patients suffering from cerebral disorders like meningitis, cranio-cerebral trauma as well as stroke (including recovery or exitus) was determined (FIG. 9). It was shown that the A-peptide level was at a very high level (above the normal level of about 35 pg/ml) at admission of the patients to the hospital. Convalescent patients having meningitis, stroke or cranio-cerebral trauma, showed a steady decrease of A-peptide concentration down to normal level. A stroke with consequent death shows significantly increased A-peptide concentrations during the whole course. The concentration of A-peptide does not decrease to normal level until exitus.

Consequence: The determination of A-peptide concentration can be used as a plasma marker for the functioning of the blood-brain barrier. As the A-peptide concentration in liquor is about 80-fold increased, as compared to the circulation, the transfer of liquor proteins into blood by the measurement of A-peptide in plasma is a signal for a present distortion of function of the blood-brain barrier. The course of A-peptide concentration allows a meaningful statement about the condition of the patient and a prognosis about the course of the disease.

EXAMPLE 10

Figure 10:
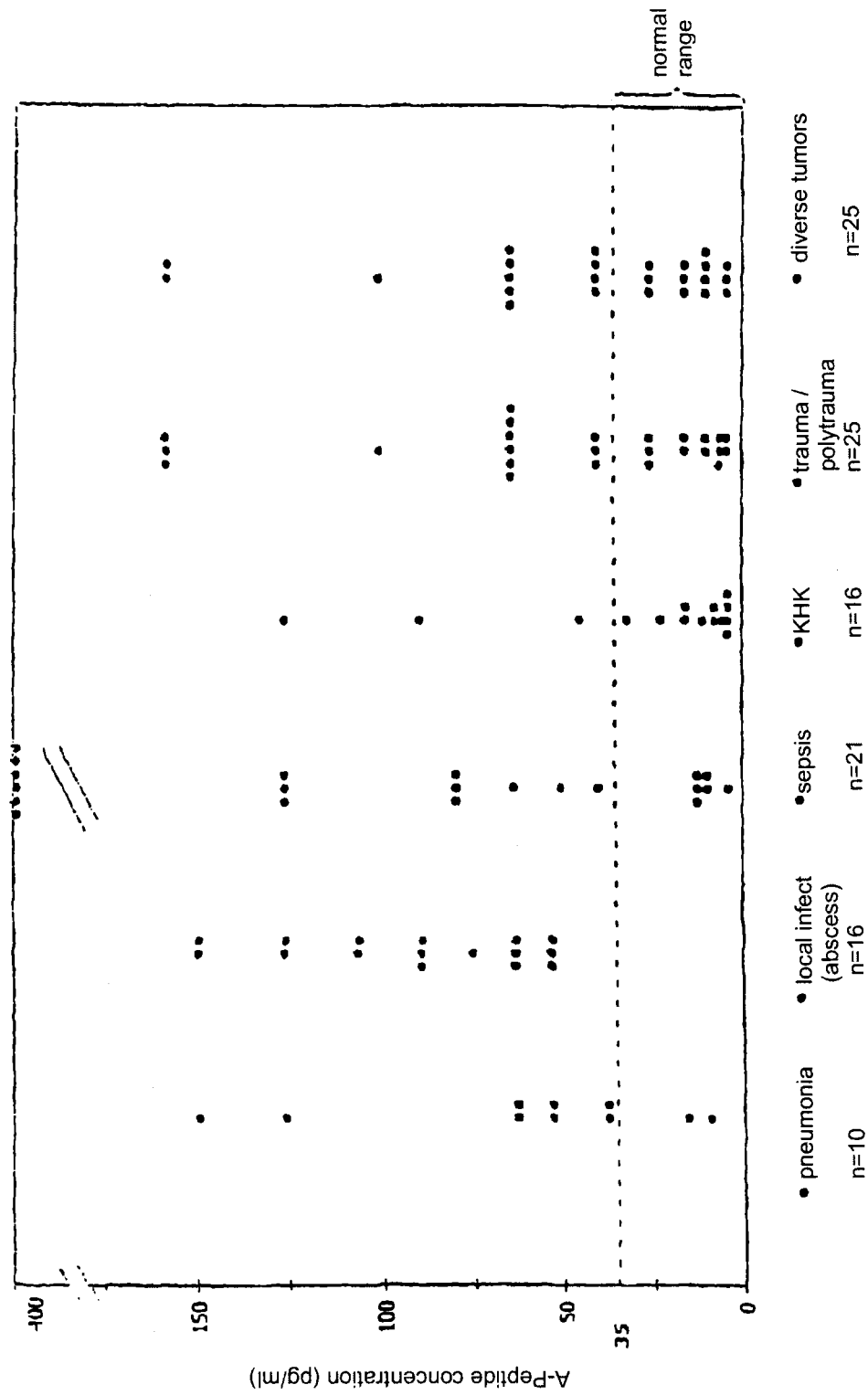
FIG. 10 shows the A-peptide concentrations in different diseases: pneumonia, local infection (abscess), sepsis, coronary heart disease, trauma and polytrauma, diverse tumors.

Determination of A-Peptide Concentration in the Circulation of Patients Suffering from Pneumonia, Local Infections, Sepsis, Coronary Heart Diseases, Trauma or Polytrauma and Different Tumors Patients suffering from inflammatory diseases, like pneumonia, local infects (abscesses) as well as sepsis, showed in parts significantly higher values (>35 pg/ml) in 80%, 100% and 72%, respectively of the cases (FIG. 10). In contrast to these results only 3 of 16 patients suffering from coronary heart diseases had a higher value than in the controls. Patients suffering from trauma and polytrauma as well as patients suffering from different tumor diseases showed an increased A-peptide concentration in 50% of the cases as compared to the control individuals.

EXAMPLE 11

A-Peptide and Simulation of Systemic Inflammation

Figure 11:
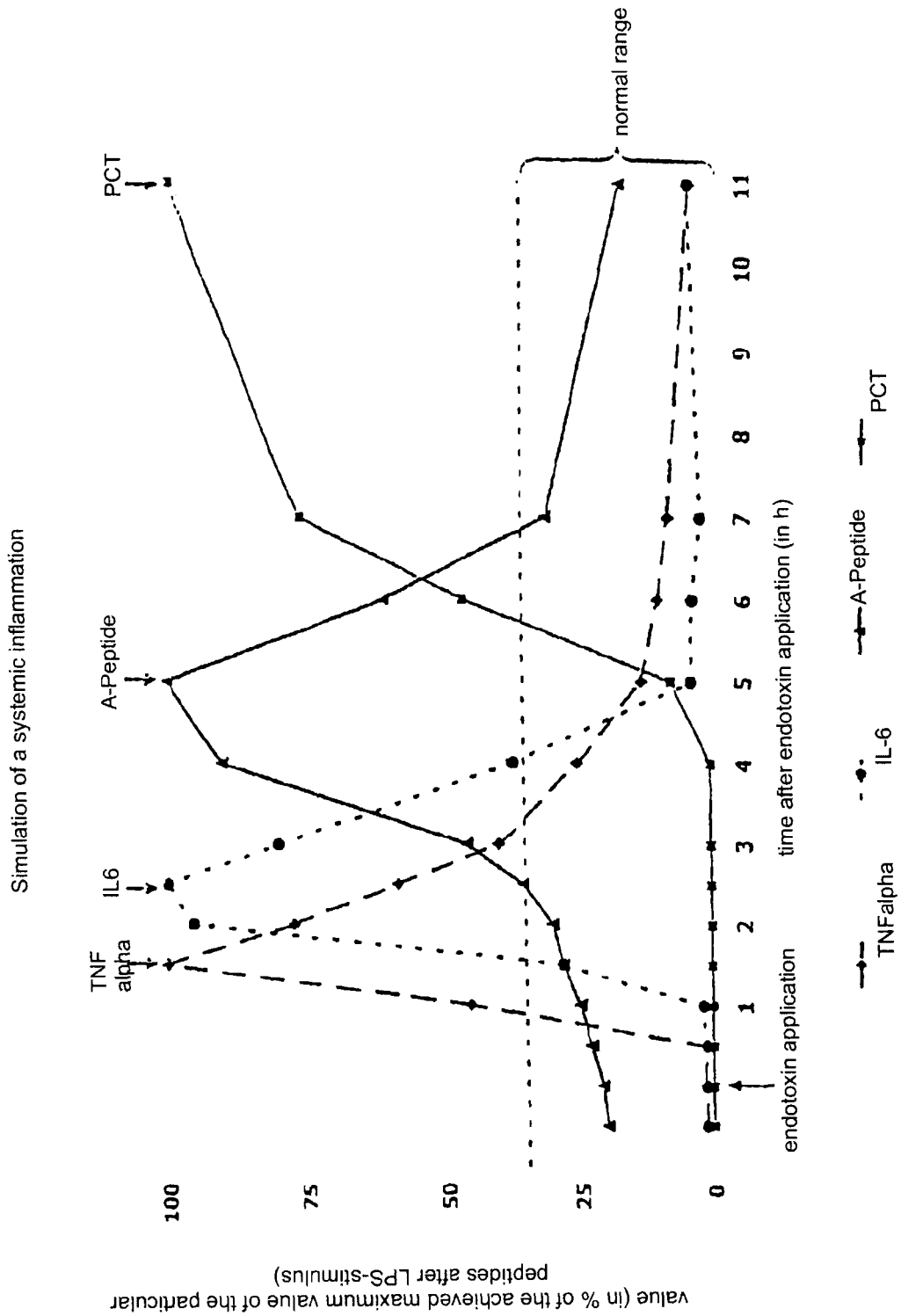
FIG. 11 shows the simulation of systemic inflammation. A-peptide-, TNF-alpha-, IL-6- and PCT-concentrations after application of endotoxin.

The standard endotoxin 0113:H10:k of *E. coli* was intravenously injected into voluntary test persons at a concentration of 4 ng/kg body weight. Blood samples were taken at different times (protocol following DANDONA et al., 1994). The determination of different parameters of inflammations (IL-6, TNFα, PCT) as well as the A-peptide in the test persons treated with endotoxin, showed a time-dependent course of concentrations of the substances in blood (see FIG. 11). First, an increase of TNFα after about 1 hour after injection of the endotoxin occurs as expected. Shortly thereafter an increase of cytotoxins IL-6 follows (about 1.5 hours after injection of the endotoxin). After 3 hours the concentrations of TNFα and IL-6 are decreasing, while now, surprisingly, an increase of A-peptide concentration occurs, which reaches the starting level after only about 7 hours. PCT shows an increase of concentration after 5 hours and steadily increases during further course. Thus the secretion of A-peptide is inducible by sole injection of endotoxin and is one event in the immune cascade between TNFα/IL-6 and PCT.

LITERATURE

DANDONA P., NIX D., WILSON M. V., ALJADA A., LOVE J., ASSICOT M., BOHUON C., (1994), Procalcitonon increase after endotoxin injection in normal subjects. Journal of Clinical Endocrinology and Metabolism 79: 1605-1608

The invention claimed is:

1. An in vitro method for measuring a concentration of protachykinin and protachykinin slice variants and fragments thereof comprising at least amino acids 1-37 of protachykinin in a sample, said method comprising:

reacting said sample with a first antibody that specific binds to an epitope within amino acids 3-21 of SEQ ID NO: 10, and a second antibody, wherein the second antibody specifically binds to a peptide consisting of the amino acid sequence DADSSIEKQVALLK (SEQ ID NO:13), wherein one of said first and second antibodies comprises a detectable label, for a time sufficient for said first and second antibodies to become bound to protachykinin, a protachykinin splice variant and/or fragments thereof in said sample, removing unbound label; and measuring a concentration of bound detectable label, wherein the concentration of bound detectable label correlates to the concentration in said sample of protachykinin and a protachykinin splice variants and/or fragments thereof comprising amino acids 1-37.

2. The method of claim 1, wherein said detectable label is a luminescent marker.

3. The method of claim 1, wherein said sample is from the circulation of a patient and is a blood sample, serum sample or plasma sample.

4. The method of claim 1, wherein at least one of said first and second antibodies is immobilized onto a solid support and the other is used for detection of the immobilized compound.

5. The method of claim 1, wherein at least one of said first and second antibodies is a monoclonal antibody.

6. The method of claim 1, wherein each of said first and second antibodies is a monoclonal antibody.

7. An in vitro method for measuring a concentration of protachykinin, protachykinin slice variants and fragments thereof comprising at least amino acids 1-37 of protachykinin in a sample from the circulation of a patient, said method comprising: reacting said sample with a first antibody that specific binds to an epitope within amino acids 3-21 of SEQ ID NO: 10, and a second antibody, wherein the second antibody specifically binds to a peptide consisting of the amino acid sequence DADSSIEKQVALLK (SEQ ID NO:13), wherein one of said first and second antibodies comprises a detectable label, for a time sufficient for said first and second antibodies to become bound to protachykinin, a protachykinin splice variant and/or fragments thereof comprising at least amino acids 1-37 of protachykinin in the sample, removing unbound label; measuring bound detectable label to determine a concentration of bound detectable label, wherein the concentration of bound detectable label correlates to the concentration of protachykinin, protachykinin splice variants and fragments thereof comprising amino acids 1-37 in said sample; and comparing said concentration of protachykinin, protachykinin splice variants and/or fragments thereof comprising at least amino acids 1-37 of protachykinin to a concentration in the normal range for healthy individuals, wherein an increased concentration of said protachykinin, protachykinin splice variants and/or fragments thereof comprising amino acids 1 to 37 in said sample indicates the presence of sepsis, tumor, cancer, Alzheimer's disease or stroke.

8. The method of claim 7, further comprising including evaluation of clinical data to determine presence, course, severity or prognosis of sepsis, tumor, cancer, Alzheimer's disease or stroke.

9. The method of claim 7, wherein an increased concentration equal to or greater than 35 pg/ml is indicative of sepsis, tumor, cancer, Alzheimer's disease or stroke.

\* \* \* \* \*

SEQUENCE LISTING

```
<160> NUMBER OF SEQ ID NOS: 14

<210> SEQ ID NO 1
<211> LENGTH: 92
<212> TYPE: PRT
<213> ORGANISM: Artificial Sequence
<220> FEATURE:
<223> OTHER INFORMATION: synthetic peptide corresponding to alpha-PPT-A
      (amino acids 1-92)

<400> SEQUENCE: 1

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Asp Ser Ser Ile Glu Lys Gln Val Ala Leu
    50                  55                  60

Leu Lys Ala Leu Tyr Gly His Gly Gln Ile Ser His Lys Met Ala Tyr
65                  70                  75                  80

Glu Arg Ser Ala Met Gln Asn Tyr Glu Arg Arg Arg
                85                  90

<210> SEQ ID NO 2
<211> LENGTH: 110
<212> TYPE: PRT
<213> ORGANISM: Artificial Sequence
```

```
<220> FEATURE:
<223> OTHER INFORMATION: synthetic peptide corresponding to beta-PPT-A
      (amino acids 1-110)

<400> SEQUENCE: 2

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Asp Ser Ser Ile Glu Lys Gln Val Ala Leu
    50                  55                  60

Leu Lys Ala Leu Tyr Gly His Gly Gln Ile Ser His Lys Arg His Lys
65                  70                  75                  80

Thr Asp Ser Phe Val Gly Leu Met Gly Lys Arg Ala Leu Asn Ser Val
                85                  90                  95

Ala Tyr Glu Arg Ser Ala Met Gln Asn Tyr Glu Arg Arg Arg
            100                 105                 110

<210> SEQ ID NO 3
<211> LENGTH: 89
<212> TYPE: PRT
<213> ORGANISM: Artificial Sequence
<220> FEATURE:
<223> OTHER INFORMATION: synthetic peptide corresponding to amino acids
      1-89 of beta PPT-A

<400> SEQUENCE: 3

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Asp Ser Ser Ile Glu Lys Gln Val Ala Leu
    50                  55                  60

Leu Lys Ala Leu Tyr Gly His Gly Gln Ile Ser His Lys Arg His Lys
65                  70                  75                  80

Thr Asp Ser Phe Val Gly Leu Met Gly
                85

<210> SEQ ID NO 4
<211> LENGTH: 76
<212> TYPE: PRT
<213> ORGANISM: Artificial Sequence
<220> FEATURE:
<223> OTHER INFORMATION: synthetic peptide corresponding to amino acids
      1-76 of beta PPT-A

<400> SEQUENCE: 4

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Asp Ser Ser Ile Glu Lys Gln Val Ala Leu
    50                  55                  60
```

```
Leu Lys Ala Leu Tyr Gly His Gly Gln Ile Ser His
 65                  70                  75
```

<210> SEQ ID NO 5
<211> LENGTH: 95
<212> TYPE: PRT
<213> ORGANISM: Artificial Sequence
<220> FEATURE:
<223> OTHER INFORMATION: synthetic peptide corresponding to aa 1-54 and
      70-110 of beta-PPT-A

<400> SEQUENCE: 5

```
Glu Glu Ile Gly Ala Asn Asp Asp Leu Asn Tyr Trp Ser Asp Trp Tyr
  1               5                  10                  15

Asp Ser Asp Gln Ile Lys Glu Glu Leu Pro Glu Pro Phe Glu His Leu
                 20                  25                  30

Leu Gln Arg Ile Ala Arg Arg Pro Lys Pro Gln Gln Phe Phe Gly Leu
             35                  40                  45

Met Gly Lys Arg Asp Ala Gly His Gly Gln Ile Ser His Lys Arg His
         50                  55                  60

Lys Thr Asp Ser Phe Val Gly Leu Met Gly Lys Arg Ala Leu Asn Ser
 65                  70                  75                  80

Val Ala Tyr Glu Arg Ser Ala Met Gln Asn Tyr Glu Arg Arg
                 85                  90                  95
```

<210> SEQ ID NO 6
<211> LENGTH: 74
<212> TYPE: PRT
<213> ORGANISM: Artificial Sequence
<220> FEATURE:
<223> OTHER INFORMATION: synthetic peptide corresponding to aa 1-74 of
      beta-PPT-A

<400> SEQUENCE: 6

```
Glu Glu Ile Gly Ala Asn Asp Asp Leu Asn Tyr Trp Ser Asp Trp Tyr
  1               5                  10                  15

Asp Ser Asp Gln Ile Lys Glu Glu Leu Pro Glu Pro Phe Glu His Leu
                 20                  25                  30

Leu Gln Arg Ile Ala Arg Arg Pro Lys Pro Gln Gln Phe Phe Gly Leu
             35                  40                  45

Met Gly Lys Arg Asp Ala Gly His Gly Gln Ile Ser His Lys Arg His
         50                  55                  60

Lys Thr Asp Ser Phe Val Gly Leu Met Gly
 65                  70
```

<210> SEQ ID NO 7
<211> LENGTH: 61
<212> TYPE: PRT
<213> ORGANISM: Artificial Sequence
<220> FEATURE:
<223> OTHER INFORMATION: synthetic peptide corresponding to aa 1-54 and
      70-76 of beta-PPT-A

<400> SEQUENCE: 7

```
Glu Glu Ile Gly Ala Asn Asp Asp Leu Asn Tyr Trp Ser Asp Trp Tyr
  1               5                  10                  15

Asp Ser Asp Gln Ile Lys Glu Glu Leu Pro Glu Pro Phe Glu His Leu
                 20                  25                  30

Leu Gln Arg Ile Ala Arg Arg Pro Lys Pro Gln Gln Phe Phe Gly Leu
             35                  40                  45

Met Gly Lys Arg Asp Ala Gly His Gly Gln Ile Ser His
```

<210> SEQ ID NO 8
<211> LENGTH: 77
<212> TYPE: PRT
<213> ORGANISM: Artificial Sequence
<220> FEATURE:
<223> OTHER INFORMATION: synthetic peptide corresponding to aa 1-54 and
      70-92 of alpha-PPT-A

<400> SEQUENCE: 8

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Gly His Gly Gln Ile Ser His Lys Met Ala
    50                  55                  60

Tyr Glu Arg Ser Ala Met Gln Asn Tyr Glu Arg Arg
65                  70                  75

<210> SEQ ID NO 9
<211> LENGTH: 50
<212> TYPE: PRT
<213> ORGANISM: Artificial Sequence
<220> FEATURE:
<223> OTHER INFORMATION: synthetic peptide corresponding to aa 1-50 of
      alpha-PPT-A

<400> SEQUENCE: 9

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly
    50

<210> SEQ ID NO 10
<211> LENGTH: 37
<212> TYPE: PRT
<213> ORGANISM: Artificial Sequence
<220> FEATURE:
<223> OTHER INFORMATION: synthetic peptide corresponding to aa 1-37 of
      alpha-PPT-A

<400> SEQUENCE: 10

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala
        35

<210> SEQ ID NO 11
<211> LENGTH: 19
<212> TYPE: PRT
<213> ORGANISM: Artificial Sequence
<220> FEATURE:
<223> OTHER INFORMATION: synthetic peptide corresponding to PSP1

-continued

```
<400> SEQUENCE: 11

Ile Gly Ala Asn Asp Asp Leu Asn Tyr Trp Ser Asp Trp Tyr Asp Ser
1               5                   10                  15

Asp Gln Ile

<210> SEQ ID NO 12
<211> LENGTH: 15
<212> TYPE: PRT
<213> ORGANISM: Artificial Sequence
<220> FEATURE:
<223> OTHER INFORMATION: synthetic peptide corresponding to PSP2

<400> SEQUENCE: 12

Lys Glu Glu Leu Pro Glu Pro Phe Glu His Leu Leu Gln Arg Ile
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: synthetic peptide corresponding to PSP3

<400> SEQUENCE: 13

Asp Ala Asp Ser Ser Ile Glu Lys Gln Val Ala Leu Leu Lys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: synthetic peptide corresponding to PSP4

<400> SEQUENCE: 14

His Lys Arg His Lys Thr Asp Ser Phe Val Gly Leu Met Gly
1               5                   10
```